United States Patent [19]

Wong

[11] Patent Number: 5,295,824
[45] Date of Patent: Mar. 22, 1994

[54] PLASTIC BRACKET WITH ADHESIVE PRIMER LAYER AND METHODS OF MAKING

[75] Inventor: Raymond F. Wong, Chino Hills, Calif.

[73] Assignee: Ormco Corporation, Glendora, Calif.

[21] Appl. No.: 941,381

[22] Filed: Sep. 4, 1992

[51] Int. Cl.$^5$ ................................ A61C 3/00
[52] U.S. Cl. ........................................ 433/9
[58] Field of Search ............... 433/9, 228.1; 427/226

[56] References Cited

U.S. PATENT DOCUMENTS

| | | | |
|---|---|---|---|
| 3,785,832 | 1/1974 | Bowen et al. | 106/35 |
| 4,010,545 | 3/1977 | Kilian et al. | 433/9 |
| 4,134,929 | 1/1979 | Stoakley et al. | 260/881 |
| 4,172,323 | 10/1979 | Orlowski | 433/9 |
| 4,228,062 | 10/1980 | Lee, Jr. et al. | 260/42.28 |
| 4,302,381 | 11/1981 | Omura et al. | 433/228.1 |
| 4,340,529 | 7/1982 | Lee, Jr. et al. | 524/105 |
| 4,479,782 | 10/1984 | Orlowski et al. | 433/9 |
| 4,553,941 | 11/1985 | Aasen | 433/228.1 |
| 4,595,598 | 6/1986 | De Luca et al. | 433/9 |
| 4,673,354 | 6/1987 | Culler | 433/217.1 |
| 4,681,538 | 7/1987 | DeLuca et al. | 433/9 |
| 4,752,221 | 6/1988 | Hanson et al. | 433/9 |
| 4,826,430 | 5/1989 | Chen et al. | 433/9 |
| 4,948,366 | 8/1990 | Horn et al. | 433/9 |
| 5,049,190 | 9/1991 | Gobel et al. | 433/212.1 |
| 5,141,436 | 8/1992 | Orlowski et al. | 433/9 |
| 5,147,202 | 9/1992 | Masuhara et al. | 433/8 |
| 5,190,795 | 3/1993 | Culler | 427/226 |

OTHER PUBLICATIONS

M. N. Coreil et al., "Shear Bond Strength of Four Orthodontic Bonding Systems", pp. 126-129.

Primary Examiner—John J. Wilson
Attorney, Agent, or Firm—Wood, Herron & Evans

[57] ABSTRACT

Plastic orthodontic brackets having an adherent acrylic adhesive primer layer on the bonding surface thereof are disclosed, as well as methods of making such brackets. Primed plastic orthodontic brackets which are shelf-stable and which obviate the need for the chairside primers commonly used by clinicians are contemplated. In a method of the present invention, a solvating mixture of solvents and acrylic monomers is applied to the bonding surface of a plastic bracket and allowed to attack (solvate) and diffuse into the plastic substrate. Thereafter the bracket is heated to volatilize the solvents and lower molecular weight monomers to thereby leave a coating or layer of acrylic material which is predominantly monomeric and is at least partially embedded in the plastic bracket. This coating acts as a primer for acrylic cements and enhances the bonding between the plastic orthodontic bracket and the tooth surface to which it is applied using acrylic adhesive cements which are themselves well known in the art.

11 Claims, 1 Drawing Sheet

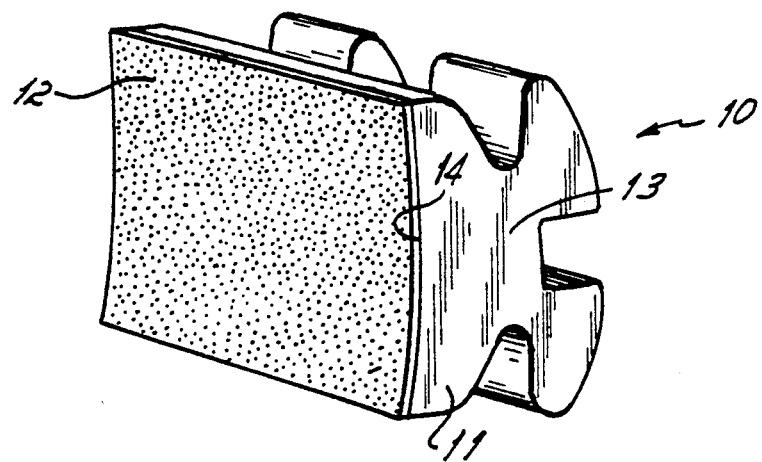

PLASTIC BRACKET WITH ADHESIVE PRIMER LAYER AND METHODS OF MAKING

FIELD OF THE INVENTION

The present invention relates to plastic orthodontic brackets and methods of making, and more particularly to plastic orthodontic brackets having an adhesive primer layer for enhancing the adhesive bond strength thereof.

BACKGROUND OF THE INVENTION

Plastic orthodontic brackets (e.g., polycarbonate) are well known in the art and provide certain advantages over metal and ceramic brackets since they are relatively light weight and aesthetically pleasing. Plastic orthodontic brackets are typically bonded directly to the enamel surfaces of teeth with an acrylic dental bonding cement, generally of the light cure or A/B dual-component, self-curing type. The bond strengths formed between acrylic cements and plastic brackets is not always sufficient to ensure that the bond will not break during the course of orthodontic treatment, either due to the forces applied by orthodontic archwires or by other external forces such as mastication.

One generally accepted approach for improving the bond strength of plastic brackets to clinically acceptable levels is to use an adhesive primer at chairside, just prior to applying the acrylic adhesive, and before bonding. This approach adds an additional step in the bonding procedure and presents a variety of drawbacks. These drawbacks include the additional chairside time required of the clinician; the added expense since the primer is a separate item which is relatively costly; and a limited working time window, on the order of minutes, for successful retention of the bracket by the bonding adhesive. Furthermore, the use of primers introduces additional complications in the bonding procedure such as the difficulty in adhesive placement and/or dilution of the adhesive paste to a consistency which causes excessive bracket drift, and the inconsistencies in bond strength which are directly related to the time/temperature dependence of diffusion of the primer into the plastic substrate. That is, since the primer acts on each bracket for a different length of time, the ultimate bond strength of each bracket may be different. Moreover, non-equivalent results are achieved depending on the type of adhesive, i.e., mix, no-mix, light-cure, etc., and adhesive primers may present an unpleasant, pungent odor and are oftentimes irritating to the patient's skin. Lastly, some of the more effective adhesive primers are being restricted in chairside use due to their suspected carcinogenic contents.

Another approach directed at enhancing the bond strength of plastic brackets with acrylic adhesives is to employ special adhesives which contain additional compounds having a high affinity to the plastic bracket substrates. Examples of this approach are found in U.S. Pat. Nos. 4,134,929, 4,228,062 and 4,340,529.

The present invention is believed to overcome the various drawbacks discussed above with respect to the known techniques for enhancing the bonding of plastic orthodontic brackets to enamel tooth surfaces.

SUMMARY OF THE INVENTION

In its broadest aspects, the present invention encompasses plastic orthodontic brackets having a thin, adherent coating or layer of an acrylic material impregnated into the bracket bonding base which enhances the bond strength of the bracket to known acrylic adhesive cements, without the drawbacks associated with chairside primers or the need for using special adhesives.

The invention further encompasses methods of making plastic orthodontic brackets having a thin adherent coating of an acrylic adhesive primer material on the bonding base thereof. In its broadest aspects, the method of making plastic brackets of the present invention comprises coating the bonding surface of a plastic bracket with a solvating mixture of solvents and acrylic monomers, allowing this mixture to attack (solvate) and diffuse into the plastic substrate, and then heating the bracket and mixture to volatilize the solvents and lower molecular weight monomers to thereby leave a coating of acrylic material which is predominantly monomeric. This coating acts as an adhesive primer and significantly enhances the bond strengths realized since the coating bonds with dental adhesives, particularly acrylic adhesives.

Suitable solvents that may be used in the practice of the present invention are benzene, chloroform, acetone, methylene chloride, M-cresol, tetrahydrofuran (1,4-epoxybutane), 1,3-dioxane, cyclohexanone, pyridine, DMF (dimethylformamide), toluene, ethyl acetate, or any other similar compounds which act as solvents for the plastic bracket composition.

Suitable acrylic monomers that are functional in the solvating mixture are compounds of dental acrylic adhesive resins such as triethylene glycol dimethacrylate, methylmethacrylate, urethane dimethacrylate, Bis GMA, and hexanediol dimethacrylate.

In the method of the present invention the solvating solvent/resin mixture is coated on the bonding surface of a plastic orthodontic bracket by any convenient method, such as by dropper or pipette dispensing onto the base surface. The mixture is allowed to solvate at ambient conditions for a period of several minutes and the bracket and solvating mixture are then subjected to moderately elevated temperatures (on the order of about 175° F. or 80° C.) to evaporate the solvent and low molecular weight components, thereby leaving a coating or layer of essentially monomeric acrylic resin at least partially embedded in the plastic substrate.

It has been advantageously determined that once the acrylic primer coating has been formed on the bonding surface of the plastic bracket, the bracket may be stored for a period of several months until ready for use, or it may be immediately bonded to a tooth, in either case utilizing an acrylic bonding adhesive without the need for any chairside primer, to achieve desirable bonding.

These and other objects and advantages of the present invention will become more apparent to persons skilled in the art upon review of the detailed description of the invention herein taken in combination with the Figure.

BRIEF DESCRIPTION OF THE DRAWING

The Figure is a perspective view of a plastic orthodontic bracket having an adhesive primer layer thereon in accordance with a preferred embodiment of the present invention.

DETAILED DESCRIPTION OF THE INVENTION

The Figure shows a preferred embodiment of an orthodontic bracket of the present invention. Bracket 10 is a plastic orthodontic bracket having a bonding base 11, a body portion 13 and an adhesive primer layer 12 adhered to and at least partially embedded in the tooth contact surface 14 of bonding base 11.

Plastic brackets made of polycarbonate are widely available in the orthodontics art and are particularly suitable for use in the present invention. Other plastic bracket materials such as polysulfone may also be used. It will be appreciated by persons skilled in the art that depending on the specific plastic material of the bracket, different solvating mixtures may be required, utilizing various solvent and monomer mixtures. Furthermore, solvent blends may produce even more superior results due to what is believed to be the "staged" or sequential solvating effect of the different solvent components in the mixture. Moreover, the addition of a peroxide and photoinitiator in the solvating mixture is preferred since it is found to provide satisfactory bonding results with virtually any type of bonding adhesive.

In the method of the present invention, a primed orthodontic bracket 10 is produced by applying a solvating mixture of solvents and acrylic resin monomers to the tooth contact surface 14 of a bracket, allowing the mixture to solvate and diffuse into the plastic substrate under ambient conditions for several minutes, and then heating the bracket and solvating mixture at a temperature in the range of about 60°-100°C. for a time period in the range of about 5 minutes to 2 hours, and more preferably in the range of about 30-60 minutes, to volatilize the solvents and lower molecular weight monomers, thereby leaving a coating 12 of acrylic material, which is predominantly monomeric, adhered to the bonding surface 14.

The following example illustrates a solvating mixture composition which is suitable for use in the practice of the present invention. This example is intended to be representative only and is not in any way to be construed as limiting the scope of the present invention.

EXAMPLE 1

The following components were mixed in the percentages shown to form a solvating mixture.

TABLE 1

| Component | Wt. % | Actual Wt. (grams) |
| --- | --- | --- |
| Urethane dimethacrylate | 5 | 0.25 |
| Triethylene glycol dimethacrylate | 3 | 0.10 |
| Ethoxylated bis phenol A dimethacrylate | 3 | 0.15 |
| Glycidylmethacrylate | 3 | 0.15 |
| Methyl methacrylate | 3 | 0.15 |
| Ionac 82 | 3 | 0.15 |
| Benzoyl peroxide | 2 phr | 0.016 |
| Camphorquinone (2,3-bornanedione) | 1 phr | 0.008 |
| Tetrahydrofuran | 20 | 1.0 |
| Methylene chloride | 20 | 1.0 |
| Cyclohexane | 20 | 1.0 |
| Toluene | 20 | 1.0 |

In Table I above, the unit designation "phr" represents parts per hundred parts resin. Additionally, "Ionac 82" is a trade name for a commercially available 50/50 copolymer manufactured and sold by Sybron Chemicals; the copolymer is poly(ethyl/methyl methacrylate).

In a preferred embodiment of a method of the present invention, a single coating of the above composition is applied to a polycarbonate plastic bracket and allowed to air dry for 5 minutes at room temperature. The solvating mixture may be dispersed by capillary action from a Pasteur pipette to coat the base. Evaporation of the solvating mixture at room temperature may take in the range of from 2-30 minutes, or until a glossy appearance is achieved. The residual solvents and low molecular weight components may be driven from the solvating mixture on the bracket base in a forced air oven for about 30 minutes at a temperature of approximately 100° C. The shear and tensile strength of the bonds achieved using a known dental adhesive such as "TRANSBOND" acrylic adhesive available from the 3M Company, or "CONCISE", which is also an acrylic adhesive available from the 3M Company, are comparable to the bonds achieved when typical chairside priming is used. TRANSBOND is a light-cure adhesive and CONCISE is a self-curing A/B type adhesive. When the light-cure TRANSBOND adhesive is used, curing is accomplished using a Demetron VCL 300 light source for approximately 30 seconds. Self-curing adhesives are allowed to cure for approximately 12-24 hours.

The bond strength data summarized in Table 2 below is from an accelerated bond stability test and indicates that the bond strengths achieved with the brackets of the present invention are repeatable even after prolonged storage of the brackets under conditions that are approximately equivalent to 18 months of room temperature storage. The data contained in Table 2 is all taken from brackets produced in accordance with the present invention which were bonded to etched bovine teeth. The brackets were produced using a solvating mixture having a formulation the same as or substantially the same as that given in Table 1. The brackets were bonded to the etched bovine teeth using 3M/Unitek TRANSBOND adhesive in a manner well known in the art for applying brackets to teeth with an acrylic cement. The "Test" brackets were stored in a gravity convection oven, air atmosphere, at 45° C.±2° C. for up to four weeks. The "Control" samples were maintained at room temperature under the normally encountered storage conditions for orthodontic brackets. The storage conditions for the Test brackets was approximately equivalent to 18 months of room temperature storage.

The shear strength of the bonds formed were measured as follows. The brackets bonded to the bovine teeth were potted in a cold cure acrylic. The acrylic blocks were held in a fixture similar to that described in an article entitled "Shear Bond Strength of Four Orthodontic Bonding Systems", *Am. J. Orthod. Dentofac. Orthop.*, 1990; 97:126-129, the contents of which are hereby incorporated herein by reference. The fixture was arranged in an Instron 1122 (Canton, Ma.) universal test machine and the cross head, fitted with a blade-type fixture for contacting the occlusal tie wings, was lowered at a rate of 1.0 mm/min until shear bond failure. The values reported in Table 2 are kilograms of load for upper right SPIRIT TM (Ormco Corporation) cuspid bracket with hook, having 0.018" slot.

As the test results suggest, there is no degradation of primer activity or bond strength, after prolonged storage and thus the primed orthodontic brackets of the present invention, as demonstrated, can be stored under normal storage/inventory conditions for extended periods of time without adversely affecting the ultimate bond strength realized.

TABLE 2

Four Week Bond Stability Test
Shear Strength (Kg)

| Week #1 | | Week #2 | | Week #3 | | Week #4 | |
|---|---|---|---|---|---|---|---|
| Test | Control | Test | Control | Test | Control | Test | Control |
| 11.0 | 6.9 | 12.8 | 6.7 | 13.2 | 13.2 | 10.2 | 7.3 |
| 7.7 | 9.6 | 10.7 | 10.3 | 10.5 | 14.4 | 11.7 | 8.3 |
| 8.4 | 9.0 | 10.6 | 10.7 | 11.2 | 9.4 | 8.1 | 7.8 |
| 10.4 | 11.4 | 8.6 | 7.1 | 9.8 | 17.1 | 12.8 | 10.9 |
| 9.0 | 10.4 | 10.3 | 20.0 | 20.5 | 8.7 | 9.0 | 7.9 |
| 9.3 | 9.4 | 10.6 | 11.0 | 13.0 | 12.6 | 10.4 | 8.4 |

Plastic brackets of the present invention, produced in accordance with the methods of the present invention, are shown to provide suitable bond strength characteristics for use in orthodontic bonding procedures while avoiding and/or overcoming the drawbacks associated with chairside adhesive primers which have been heretofore used prior to applying acrylic adhesives to bond plastic brackets to a patient's teeth. The various examples given herein are intended to be exemplary of compositions suitable for use in the practice of the present invention, they are not intended to be limiting in any way. It will be appreciated that variations in the composition of the solvating mixture which results in primed brackets having suitable bonding characteristics clearly fall within the scope of and are contemplated by the present invention as it is defined in the appended claims.

What is claimed is:

1. A shelf-stable plastic orthodontic bracket, comprising:
    a body portion,
    a bonding base made of a plastic material and having a tooth contact surface, and
    a monomeric adhesive primer layer adhered to and solvated into said tooth contact surface, said primer layer is shelf stable and retain to efficacy to enhance the bond strength of said bracket with a dental adhesive even after prolonged storage of said bracket for up to at least several weeks.

2. A plastic orthodontic bracket of claim 1 wherein said bonding base is polycarbonate.

3. A plastic orthodontic bracket of claim 2 wherein said monomeric primer layer comprises an acrylic material.

4. A shelf-stable plastic orthondontic bracket, comprising:
    a body portion,
    a bonding base integral with said body portion which is made of a plastic material and has a tooth contact surface, and
    a monomeric, acrylic adhesive primer layer, said primer layer is adhered to and solvated into said tooth contact surface, is shelf stable, and retains its efficacy to enhance the bond strength of said bracket with a dental adhesive even after prolonged storage of said bracket for cup to at least several weeks.

5. A method of making a shelf-stable plastic orthodontic bracket having an adhesive primer layer, comprising:
    applying a solvating mixture containing solvents and monomers to the tooth contact surface of a plastic bracket and allowing said mixture to solvate into said plastic tooth contact surface for a predetermined period of time, and
    heating the bracket and solvating mixture to volatilize solvents and lower molecular weight monomers in said solvating mixture to thereby form a monomeric adhesive primer layer adhered to and solvated into said tooth contact surface, said primer layer being shelf-stable and retaining is efficacy to enhance the bond strength of said bracket with a dental adhesive even after prolonged storage of said bracket for up to at least several weeks.

6. A method of claim 5 wherein said bracket bonding base is polycarbonate and said solvating mixture contains acrylic monomers.

7. A method of claim 5 wherein said predetermined period of time for allowing said solvating mixture to solvate and diffuse into said tooth contact surface is in the range of about 2-30 minutes.

8. A method of claim 5 wherein said bracket and solvating mixture is heated to a temperature in the range of about 60°-100° C. for a time period in the range of about 5 minutes to 2 hours.

9. A shelf-stable plastic orthodontic bracket produced according to the method of claim 5.

10. A method of making a shelf-stable, plastic orthodontic bracket having an adhesive primer layer, comprising:
    applying a solvating mixture containing solvents and acrylic monomers to the tooth contact surface of a polycarbonate plastic bracket and allowing said mixture to solvate into said plastic tooth contact surface for a predetermined period of time in the range of about 2-30 minutes, and
    heating the bracket and solvating mixture to a temperature in the range of about 60°-100° C. for a time period in the range of about 5 minutes to 2 hours to volatilize solvents and lower molecular weight monomers in said solvating mixture to thereby form a monomeric adhesive primer layer adhered to and solvated into said tooth contact surface, said primer layer being shelf-stable and retaining its efficacy to enhance the bond strength of said bracket with a dental adhesive even after prolonged storage of said bracket for up to least several weeks.

11. A shelf-stable plastic orthodontic bracket produced according to the method of claim 10.

* * * * *

UNITED STATES PATENT AND TRADEMARK OFFICE
CERTIFICATE OF CORRECTION

PATENT NO. : 5,295,824
DATED : March 22, 1994
INVENTOR(S) : Raymond F. Wong

It is certified that error appears in the above-indentified patent and that said Letters Patent is hereby corrected as shown below:

Column 5, line 38, please replace the first occurrence of "to" with --its--.

Column 6, line 1, please replace "cuup" with --up--.

Signed and Sealed this

Sixth Day of September, 1994

*Attest:*

BRUCE LEHMAN

*Attesting Officer*  *Commissioner of Patents and Trademarks*